(12) United States Patent
Riehm

(10) Patent No.: US 6,323,382 B1
(45) Date of Patent: *Nov. 27, 2001

(54) $C_8$ ALKYL AROMATIC HYDROCARBON ISOMERIZATION PROCESS

(76) Inventor: Roger A. Riehm, 309 Rice St., Elmore, OH (US) 43416-0702

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/564,942

(22) Filed: Nov. 30, 1995

Related U.S. Application Data

(63) Continuation of application No. 08/224,155, filed on Apr. 7, 1994, now abandoned.

(51) Int. Cl.[7] ...................................................... C07C 5/22
(52) U.S. Cl. ............................................ 585/482; 585/481
(58) Field of Search .................................... 585/477, 478, 585/480, 481, 482

(56) References Cited

U.S. PATENT DOCUMENTS

| | | | |
|---|---|---|---|
| 3,538,173 | 11/1970 | Berger et al. | 260/668 |
| 3,553,276 | 1/1971 | Berger et al. | 260/668 |
| 4,139,571 | 2/1979 | Riehm | 260/668 A |
| 4,300,014 * | 11/1981 | Yamasaki et al. | 585/481 |
| 4,469,909 * | 9/1984 | Chester et al. | 585/481 |
| 4,482,773 * | 11/1984 | Chu et al. | 585/481 |
| 4,697,039 * | 9/1987 | Schmidt | 585/481 |

* cited by examiner

*Primary Examiner*—Bekir L. Yildirim
(74) *Attorney, Agent, or Firm*—Marshall & Melhorn, LLC

(57) ABSTRACT

A process for activating and maintaining a catalyst used in isomerizing a $C_8$ alkyl aromatic hydrocarbon containing feedstock. The activation of the catalyst is accomplished through the oxidation and reduction of the metal component in the catalyst. The oxidation of the metal component is accomplished by circulating a stream of nitrogen containing about one percent oxygen at a temperature of about 480° C. The oxidized metal component is then reduced by circulating pure hydrogen through the reactor over a range of specific pressure and temperature conditions. On completing the activation of the catalyst a feedstock is then circulated through the catalyst to isomerize a $C_8$ alky aromatic feedstock. The positive activity of the catalyst is maintained during the isomerization process by recycling a hydrogen-rich fraction having a high hydrogen purity. The purity of the hydrogen-rich fraction is maintained by increasing the system pressure of the recycle stream high enough to cause a phase change of the light hydrocarbon impurities from a vapor to a liquid.

13 Claims, No Drawings

C₈ ALKYL AROMATIC HYDROCARBON ISOMERIZATION PROCESS

This application is a continuation of U.S. application Ser. No. 08/224,155, filed Apr. 7, 1994, now abandoned.

1. FIELD OF THE INVENTION

This invention relates to a $C_8$ alkyl aromatic isomerization process. More particularly, this invention relates to an improved process to maintain the positive activity of a catalyst for isomerization of the $C_8$ alkyl aromatic for improved yield of desired $C_8$ alkyl aromatics.

2. BACKGROUND OF THE INVENTION

Processes for the production of various $C_8$ alkyl isomers are of importance within the petroleum and petrochemical industries. This interest is a result of the demand for specific isomers, in particular, p-xylene and o-xylene. P-xylene is a valuable chemical feedstock which may be used in the synthesis of polyesters. The p-xylene may be derived from mixtures of $C_8$ alkyl aromatics separated from such raw materials as petroleum napthas and pyrolysis distillates, usually by selective solvent extraction. The $C_8$ alkyl aromatics in such mixtures and their properties are as follows:

|  | Freezing Point (° F.) | Boiling Point (° F.) | Density (lbs/U.S. gallon) |
| --- | --- | --- | --- |
| Ethylbenzene | −139.0 | 277.0 | 7.26 |
| p-xylene | 55.9 | 281.0 | 7.21 |
| m-xylene | −54.2 | 282.4 | 7.23 |
| o-xylene | −13.3 | 292.0 | 7.37 |

The $C_8$ alkyl aromatic fractions from the above identified sources may vary quite widely in composition, but usually comprise about 10–32 weight percent ethylbenzene, with the balance, xylenes, being divided approximately as 50 weight m-xylene and 25 weight percent each of p-xylene and o-xylene.

Thus, a mixed $C_8$ alkyl aromatic stream may be fed to one or more separation steps or units, e.g., crystallization, adsorption, superfractionation and the like, for separation of one or more specific $C_8$ alkyl aromatic isomers. The remaining $C_8$ alkyl aromatic material is often fed to an isomerization reaction zone wherein the concentration of the desired isomer or isomers is replenished. The effluent, or at least a portion of the effluent, from the isomerization reaction zone is then fed to the separation unit for recovery of the desired isomer or isomers.

In one particular $C_8$ alkyl aromatic isomerization process, the isomerization is commonly affected by contacting the hydrocarbon in admixture with hydrogen at isomerization conditions with a dual function catalyst possessing both hydrogenation and cracking activities thereby effecting the desired isomerization reaction. By contacting the $C_8$ alkyl aromatic with the catalyst at isomerization conditions, $C_8$ naphthalenes, toluene and $C_9+$ aromatics, among other by-products, are often produced. It has been found that such $C_8$ naphthenes are beneficially maintained in the $C_8$ alkyl aromatic stream sent to the separation zone and then recycled back to the isomerization zone to improve the yield of the specific or desired $C_8$ aromatic isomer. A number of patents have disclosed processing schemes to take advantage of the beneficial effects of recycling $C_8$ naphthenes to a $C_8$ alkyl aromatic isomerization zone. Among these patents are U.S. Pat. Nos. 3,538,173 and 3,553,276.

Although many prior art processes have talked in terms of providing improved yields of the specific or desired alkyl aromatic isomer, it would be clearly advantageous to provide still further improvement in $C_8$ alkyl aromatic isomer yields. Therefore, one of the objects of the present invention is to provide an improved process for isomerizing a $C_8$ alkyl aromatic hydrocarbon-containing feedstock. Another object of the present invention is to provide a process for maintaining the positive activity of a catalyst to isomerize a mixed composition of $C_8$ alkyl aromatics isomers to one or more desired isomers. A still further object of the present invention is to provide a $C_8$ alkyl aromatic isomerization process with reduced xylene ring loss. Yet another object of the present invention is to provide a process for converting ethylbenzene to xylene with reduced xylene ring loss by limiting the temperature of the reduction step in the activation of the catalyst to no more than 340 degrees celsius. Yet another object of the present invention is to provide an improved process for isomerizing a $C_8$ alkyl aromatic hydrocarbon-containing feedstock that is simple and economical to operate.

The present invention is improvement to the xylene isomerization process known as "Octafining II" and described in U.S. Pat. No. 4,139,571. Briefly, the Octafining II process employs a noble metal catalyst in combination with a p-xylene recovery process and/or o-xylene recovery by fractionation.

Further features and other objects and advantages of the present invention will become apparent from the following detailed description.

3. SUMMARY OF THE INVENTION

Briefly, according to the present invention, there is provided a process for isomerizing a $C_8$ alkyl aromatic hydrocarbon-containing feedstock. The process includes the steps of (1) providing a catalyst including at least one metal component; (2) activating the catalyst by oxidizing the metal component of the catalyst and then reducing the oxidized metal component at a temperature range of 340 degrees celsius at atmospheric pressure to 315 degrees celsius at 12 kg/cm² G. to yield a catalyst that gives the desired degree of isomerization with a lower ring loss of the more valuable xylene isomers; (3) contacting the feedstock in at least one isomerization zone with the catalyst and being effective to promote $C_8$ alkyl benzene isomerization at isomerization conditions in the presence of hydrogen at isomerization conditions to isomerize at least a portion of the $C_8$ alkyl aromatic hydrocarbons and to produce an effluent; (4) separating the effluent to form a hydrogen-rich fraction, a first hydrocarbon-rich fraction containing benzene and toluene and having a lower average molecular weight relative to $C_8$ alkyl aromatic, and a second fraction enriched in $C_8$ alkyl aromatic content relative to the effluent; (5) subjecting at least a portion of the first hydrocarbon-rich fraction to the contacting of step (3); and (6) recovering at least one $C_8$ alkyl aromatic product from the second fraction. The metal component is oxidized by soaking the catalyst in a hot stream of nitrogen containing approximately 1 weight percent oxygen to form metal oxide. The metal oxide is then reduced with pure hydrogen to metal crystallites.

The positive activity of the catalyst may be maintained by preventing accelerated coke formation by recycling hydrogen rich gas to protect the catalyst. The hydrogen gas purity is maintained by increasing the hydrogen partial pressure within the process. The hydrogen partial pressure within the process is increased by increasing the process pressure. The process pressure is increased increasing the rate of hydrogen rich makeup gas with no purge of recycled hydrogen rich gas. Hydrogen purity and hydrogen partial pressure are maintained by controlling the system pressure. The hydrogen partial pressure regulates the rate of isomerization and can be controlled with no purge of valuable hydrogen gas. The light hydrocarbon impurities produced as byproducts of the isomerization reaction are purged from the system as liquid products in the first hydrocarbon-rich fraction.

4. DETAILED DESCRIPTION OF THE PREFERRED EMBODIMENTS

The present invention involves a process for isomerizing a $C_8$ alkyl aromatic hydrocarbon-containing feedstock, p-xylene, m-xylene, o-xylene and ethylbenzene in a non-equilibrium mixture. This process comprises the steps of (1) contacting the feedstock with an isomerization catalytic composite in the presence of hydrogen at isomerization conditions to isomerize at least a portion of the $C_8$ alkyl aromatic hydrocarbons and to produce an effluent; (2) separating the effluent to form a hydrogen-rich gaseous fraction, a first hydrocarbon-rich fraction containing toluene and having a lower average molecular weight relative to $C_8$ alkyl aromatic content, and a second fraction enriched in $C_8$ alkyl aromatic content relative to the effluent; (3) subjecting at least a portion of the first hydrocarbon-rich fraction to the contacting of step (1); and (4) recovering at least one $C_8$ alkyl aromatic product from the second fraction.

Among the reactions which often occur in the isomerization zone of the present process are the production of $C_8$ naphthenes and toluene. These naphthenes are produced, for example, by the hydrogenation of the $C_8$ alkyl aromatics, some naphthenes being subsequently isomerized. Toluene is often produced by disproportionation of $C_8$ alkyl aromatics, as well as other cracking-type reactions.

In one preferred embodiment, the process of the present invention is as follows. A hydrocarbon feedstock comprising $C_8$ alkyl aromatic hydrocarbons, i.e., p-xylene, o-xylene, m-xylene and ethylbenzene, in a non-equilibrium mixture is contacted with a catalytic composite in the presence of hydrogen at isomerization conditions in at least one reaction zone. The reaction zone effluent is passed to a gas separation zone, e.g., flash drum and the like, wherein a hydrogen-rich gaseous fraction is removed from the effluent. This hydrogen-rich gaseous fraction is recycled back to the isomerization zone along with makeup hydrogen rich gas in the presence of which the isomerization reaction takes place. The remainder of the effluent from this gas separation zone proceeds as a liquid until it is flashed to a lower pressure to a second separation zone, e.g., distillation tower and the like, wherein a first hydrocarbon-rich fraction containing toluene, e.g., which is produced in the isomerization reaction zone, and having a lower average molecular weight relative to $C_8$ alkyl aromatics is recovered. The remainder of the effluent, which comprises a second fraction enriched in $C_8$ alkyl aromatic content relative to the total isomerization zone reactor effluent is sent to further separation zones, e.g., distillation, crystallization, adsorption, superfractionation and the like, for recovery of at least one desired $C_8$ alkyl aromatic isomer product. Preferably, at least a portion of the $C_9$ and heavier hydrocarbon material, e.g., produced in the isomerization zone, is removed from the effluent. At least a portion of the $C_8$ alkyl aromatic hydrocarbons remaining after recovery of the desired isomer product or products is preferably recycled to the isomerization zone for further isomerization. At least a portion of the first hydrocarbon-rich fraction is sent to the isomerization reaction zone. By sending at least a portion of the first hydrocarbon-rich fraction to the isomerization reaction zone, improved yields of specific or desired $C_8$ alkyl aromatic hydrocarbon isomers are obtained as well as more efficient and complete $C_8$ alkyl aromatic isomerization. In one embodiment, the first hydrocarbon-rich fraction also contains $C_8$ naphthenes.

In one specific embodiment, the remainder of the isomerization reaction zone effluent from the gas separation zone is fed to a distillation tower system, e.g., including a column or columns, and associated equipment such as reboilers, condensers, coolers, product collection zones, pumps and the like, wherein lower boiling materials are concentrated in the overhead product from such tower. The overhead product of this tower may, for example, by controlling the tower operating pressure, be maintained totally or substantially totally in the liquid phase. However, in a preferred embodiment, the distillation tower is controlled or operated so that a portion of the overhead product leaves the system as a gaseous material. In this embodiment, at least a portion of the liquid overhead product of this tower is routed to the isomerization zone. In an additional embodiment, the first hydrocarbon-rich fraction which is at least partially routed to the isomerization zone may be taken as a side stream product from this distillation tower. In any event, the first hydrocarbon-rich fraction may be characterized as containing toluene, and possibly $C_8$ naphthenes, and having a lower average molecular weight relative to $C_8$ alkyl aromatics. In a preferred embodiment, this first hydrocarbon-rich fraction is substantially free of $C_8$ alkyl aromatic hydrocarbons, e.g., contains less than about 5%, more preferably less than about 1%, by weight of $C_8$ alkyl aromatics.

The first hydrocarbon-rich fraction may further contain $C_1$ to $C_8$ paraffins such as methane, ethane, propane, butane, pentane, hexane, heptane, and octane having various structural configurations; $C_5$, $C_6$ and $C_7$ naphthenes and benzene. Preferred component concentrations in the first hydrocarbon-rich fraction are as follows:

0% to about 40% by weight $C_1$ to $C_4$ components,

0% to about 40% by weight $C_5$ to $C_8$ paraffins, about 1% to about 20% by weight of $C_5$ to $C_7$ naphthenes, 0% to about 50% by weight $C_8$ naphthenes, about 1% to about 20% by weight benzene, and about 3% to about 70% by weight of toluene.

Preferably, the separation zone, e.g., distillation tower or towers, which produces the first hydrocarbon-rich fraction is designed so that a substantial portion of the toluene and $C_8$ naphthenes in the feed to this separation zone, e.g., in the isomerization zone feedstock and produced in the isomerization reaction zone, remains with the material which is sent to further processing, e.g., the bottoms product from the distillation tower. Thus, the amount of toluene in the first hydrocarbon-rich fraction is preferably a portion, more preferably more than about 10% and still more preferably more than about 20%, of the total toluene in the feed to this separation zone. The amount of $C_8$ naphthenes in the first hydrocarbon-rich fraction, if any, is preferably a portion, more preferably less than about 90% and still more preferably less than about 80%, of the total $C_8$ naphthenes in the feed to this separation zone. Preferably, only a portion, e.g., at least about 30%, more preferably at least about 40% and still more preferably, at least about 50% by weight of the first hydrocarbon-rich fraction is routed to the isomerization reaction zone. A portion of this material is preferably removed from the process in order to control the level of toluene and/or lighter components in the reaction zone to an economically reasonable level. Since, in a preferred embodiment, this first hydrocarbon-rich fraction also contains C$_8$ naphthenes, C$_8$ naphthenes are removed from the process by removing a portion of the first hydrocarbon-rich fraction. This loss in C$_8$ naphthenes in the first hydrocarbon-rich fraction detrimentally affects the yields of specific desired C$_8$ alkyl aromatic isomers and, therefore, should be minimized, e.g., as described above.

The C$_8$ naphthenes include various alkylcyclopentanes and alkylcyclohexanes such as 1,1,3-trimethylcyclopentane, 1,1,2-trimethylcyclopentane, the 1,2,4-trimethylcyclopentanes, the 1,2,3-trimethylcyclopentanes, 1,1-dimethylcyclohexane, 1,4-dimethylcyclohexane, the methyl-ethylcyclopentanes, etc. It is advantageous to recycle at least a portion of these naphthenic hydrocarbons present in the isomerization zone effluent back to the isomerization reactor thereby minimizing aromatic hydrocarbon losses to naphthenes, since it appears that these naphthenes exist in equilibrium with the C$_8$ alkyl aromatics.

The present process involves at least one isomerization catalytic composite. Such catalysts include at least one hydrogenation-dehydrogenation component, preferably selected from the group consisting of Group VI metal components, Group VII metal components, Group VIII metal components and mixtures thereof. These metallic components are usually combined with, e.g., impregnated on, a carrier such as at least one acidic inorganic oxide, e.g., alumina, silica-alumina and the like, the faujasites, mordenite, etc., or various combinations thereof, preferably in an amount, calculated on an elemental basis, of about 0.05% to about 30% by weight of the catalyst composite. In addition, the catalysts may contain small amounts, e.g., about 0.1% to about 5.0% by weight of the catalyst, of halogen such as chlorine and/or fluorine, to enhance the catalytic benefit of the catalyst or, even further, such halogens may be continuously passed to the isomerization reaction zone in admixture with the hydrogen and/or hydrocarbon feedstock.

The preferred catalytic materials used in this invention include crystalline aluminosilicates, of either natural or synthetic origin, having an ordered internal structure. These materials are possessed of high surface area per gram and are microporous. The ordered structure gives rise to a definite pore size, related to the structural nature of the ordered internal structure. Several forms are commercially available. For example, a 5A material indicates a material of A structure and a pore size of about 5A diameter. A 13X material is one of X faujasite structure and 10–13 A pore diameter, and so on. There are also known materials of Y faujasite structure, and others. Many of these materials may be converted to the H or acid form, wherein a hydrogen occupies the cation site. For example, such a conversion may be had with many such materials by ion-exchange with an ammonium ion followed by heating to drive off NH$_3$, or by controlled acid leaching. In general, the H form is more stable in materials having higher Si/Al ratios, such as about 2.5/1 and above. The aluminosilicate concentration is preferably in the range of about 1% to about 75%, more preferably about 5% to about 50%, by weight of the total isomerization catalytic composite.

One material having substantial C$_8$ alkyl aromatic isomerization catalytic activity is H mordenite. Mordenite is a material occurring naturally as the hydrated sodium salt corresponding to:

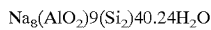

Na$_8$(AlO$_2$)9(Si$_2$)40.24H$_2$O

This mordenite material may be leached with dilute hydrochloric acid to arrive at an H or acid form. Preferably, the mordenite material useful in the present invention contains more than about 50 percent in the acid form.

Another type of high activity isomerization catalyst may be prepared by using conventional 13X molecular sieve, e.g., such as is described in U.S. Pat. No. 2,882,244. This material may be base exchanged with a solution of rare-earth chlorides (containing 4 percent of RECl$_{3.6}$H$_2$O) at about 1800–2000 F. to remove sodium ions from the aluminosilicate complex and replace at least some of them with the chemical equivalent of rare-earth ions. After washing free of soluble material and drying, there is produced an REX aluminosilicate containing about 1.0–1.5 percent (wt.) of sodium and about 20 to 30 percent (wt.) of rare earth ions calculated as RE$_2$O$_3$.

Materials incorporating both metal base exchange and an ammonia base exchange may be obtained by treating simultaneously or serially with metal salts and ammonia, followed by heating, to get metal-hydrogen forms of the crystalline aluminosilicate.

Similar preparations having isomerization catalytic activity may include a variety of crystalline aluminosilicates, such as Y faujasites, gmelinite, chabazite, and the like. For a fuller discussion of the nature of aluminosilicates and their method of preparation attention is also directed to U.S. Pat. No. 3,033,778 to Frilette, and U.S. Pat. No. 3,013,989 to Freeman.

The preferred aluminosilicate-containing catalysts may be varied within wide limits as to aluminosilicate employed, cation character and concentration, and added components incorporated by precipitation, ion exchange, adsorption and the like. Particularly important variables are silica to alumina ratio, pore diameter and spatial arrangement of cations. The cations may be protons (acid) derived by base exchange with solutions of acids or ammonium salts, the ammonium ion decomposing on heating to leave a proton. Polyvalent metals may be supplied as cations, as such or as spacing or stabilizing agents in acid alumino-silicates for stabilization. In addition to the rare-earth metals mentioned above, other suitable cations for exchange in the aluminosilicates include, for example, magnesium, calcium, manganese, cobalt, zinc, silver and nickel.

The preferred crystalline aluminosilicates are the hydrogen and/or polyvalent metal forms of synthetically prepared faujasite and mordenite, particularly, mordenite having an effective diameter of about 6 angstrom units (A) and a mole ratio of silica to alumina of about 6 to about 15, and more particularly, the hydrogen form of mordenite. A particularly preferred crystalline aluminosilicate is acid-extracted mordenite having an SiO$_2$/Al$_2$O$_3$ ratio above about 10. One method of forming this material involves subjecting the ordinary form of mordenite having a SiO$_2$/Al$_2$O$_3$ of about 9 to 10 to the action of a strong acid such as hydrochloric acid, sulfuric acid, hydrofluoric acid and the like, at conditions effecting the removal or extraction of at least a portion of the aluminum from the mordenite. Typically, this procedure can be used to obtain mordenite having a SiO$_2$/Al$_2$O$_3$ ratio of about 11 or more.

One preferred class of crystalline aluminosilicates useful in the present invention are those materials in which hydrogen, polyvalent metals and mixtures thereof occupy at least about 50%, and more preferably, at least about 90%, of the cation positions of the aluminosilicate structure.

The presently useful isomerization catalytic composites preferably include at least one platinum group metal component. In addition, in some cases, the composite may contain a rhenium component. It is intended to include as a platinum group metals, platinum, palladium, ruthenium, iridium, rhodium and osmium. The platinum group metallic component, such as platinum or palladium, may exist within the final catalytic composite as a compound such as an oxide, sulfide, halide, etc., or as an elemental metal. Generally, the amount of the platinum group metallic component present in the final catalyst is small compared to the quantities of the other components combined therewith. In fact, the platinum group metallic component preferably comprises about 0.02% to about 3.0% by weight of the final catalytic composite, calculated on an elemental basis. Excellent results are obtained when the catalyst contains about 0.2 percent to about 1.0 percent by weight of the platinum group metal.

The catalyst metallic components, e.g., platinum group metallic component, may be incorporated in the catalytic composite in any suitable manner such as co-precipitation or cogellation with the carrier material, ion-exchange with the carrier material, or impregnation either before, during or after incorporation of the aluminosilicate component into the carrier material and either after or before calcination of the carrier material, etc. One preferred method of incorporating the platinum group metal component involves the utilization of water soluble compounds of the platinum group metals with which the carrier material is combined by an impregnation technique. Thus, the platinum group metal may be added to the carrier material by co-mingling the latter with an aqueous solution of chloroplatinic acid. Other water-soluble compounds of platinum may be employed as impregnation solutions and include ammonium chloroplatinate, platinum chloride, dinitro diamino platinum, etc. In one preferred embodiment, the platinum group metal is incorporated, e.g., by impregnation, into the carrier material prior to the alumino silicate being added. In this embodiment, the crystalline aluminosilicate component of the final catalyst is preferably substantially free of platinum group metal. In another preferred embodiment, the carrier material is impregnated after it has been calcined in order to minimize the risk of washing away the valuable platinum metal compounds. However, in some cases, it may be advantageous to impregnate the carrier or support when it is in a gelled state. Following the impregnation, the resulting impregnated support is dried. Additional components, e.g., crystalline aluminosilicates, if any, can be incorporated into the impregnated carrier material using conventional techniques. The presently useful catalysts may be macroformed into particles using conventional techniques such as extrusion, tabletting, spheroidizing and the like. These catalysts are also subjected to high temperature calcination, preferably at temperatures of about 600° F. to about 1500° F. for a period of time in the range of about 0.5 hours to about 20 hours or more.

In one embodiment, the presently useful catalysts include a rhenium component. This component may be present as an elemental metal, as a chemical compound, such as the oxide, sulfide, halide, or in a physical or chemical association with the carrier material and/or the other components of the catalyst. Generally, the rhenium component is utilized in an amount sufficient to result in a final catalytic composite containing about 0.02 to about 1.0 wt. percent rhenium, calculated as an elemental metal. The rhenium component may be incorporated in the catalytic composite in any suitable manner and at any stage in the preparation of the catalyst. One preferred procedure for incorporating the rhenium component involves the impregnation of the carrier material either before, during, or after the other components referred to above are added. The impregnation solution can, in some cases, be an aqueous solution of a suitable rhenium salt such as ammonium perrhenate, sodium perrhenate, potassium perrhenate and the like salts. In addition, aqueous solutions of rhenium halides such as the chlorides may be used if desired; however, the preferred impregnation solution is an aqueous solution of perrhenic acid. The rhenium component can be impregnated either prior to, simultaneously with, or after the platinum group metallic component is added to the carrier material. However, best results are achieved when the rhenium component is impregnated simultaneously with the platinum group metallic component.

Typical reaction conditions utilized in the present process include temperatures of about 50° F. to about 1200° F., preferably about 400° F. to about 1000° F., weight hourly space velocities (weight of hydrocarbons passed per hour per weight of catalyst) of about 0.1 to about 40, preferably about 0.5 to about 8, reaction pressures of about atmospheric to about 100 atmospheres or more, preferably about 5 atmospheres to about 50 atmospheres, and hydrogen to $C_8$ alkyl aromatic hydrocarbon mole ratios of about 0.5:1 to about 25:1 or more, preferably about 3:1 to about 15:1. In a preferred embodiment, the reactants in the isomerization zone are substantially vaporous.

In accordance with the present invention, further improved yields of desired $C_8$ alkyl aromatic isomers may be obtained by maintaining the positive activity of the catalyst composite in the isomerization zone. As previously noted the catalyst has both a dehydrogenation function and an isomerization function. The dehydrogenation function is conferred by the metal component of the catalyst and the second function is conferred by the acidic properties of the catalyst. It will be appreciated that the acidic function of the catalyst also promotes certain undesirable reactions during the isomerization process such as cracking or formation and deposit of carbon or coke on the catalyst which results in a rapid deactivation of the catalyst and a significant decrease in the yield of the desired resultant products and in the formation of hydrogen contaminated with hydrocarbons such as methane.

In the activation of the catalyst, the catalyst is first oxidized by soaking the catalyst in a hot stream of nitrogen containing approximately 1 weight percent (or equivalent to 1 percent by volume) oxygen at a temperature starting at ambient and completing the soaking at temperatures up to 480 degrees celsius for a sufficient time to convert all of the metallic components to the corresponding oxide form. Preferably, the temperature increase is limited to 427° C. to prevent degradation of the carrier for the catalyst. The resultant oxidized catalyst is then subjected to a reduction step prior to its use in the isomerization process. This step is designed to selectively reduce the metal component to the elemental metallic state and to ensure a uniform and finely divided dispersion of the metallic component throughout the catalyst. Reduction of the oxidized catalyst may be performed by contacting the oxidized catalyst with pure hydrogen to reduce substantially all of the metallic component to the elemental metallic state. During this reduction step some of the Bronsted acid sites of the catalyst are converted to Lewis acid sites with the loss of water from the catalyst crystal structure. It is appreciated that excessive temperature and hydrogen partial pressure will convert more Bronsted sites to Lewis Acid sites thereby imparting more cracking activity resulting in an excessive ring loss of the mixed xylene feed instead of the desired isomerization activity.

To maintain the positive activity of the catalyst to isomerize mixed xylene feed depleted in one or more of the $C_8$ alkyl aromatic isomers to a mixture that approaches an equilibrium mixture of m-xylene, o-xylene and p-xylene with a minimum of xylene ring loss it has been found that by limiting the temperature of the reduction step to no more than 340 degrees at ambient pressure down to 315 degrees celsius at 12 kg/cm² G. there was little or no evolution of water other than that accounted for in the reduction of metal oxides. It is believed that by limiting the temperature at which the evolution of water occurs, the Bronsted acid sites are not converted to Lewis acid sites such that the cracking activity of the catalyst is repressed by the reduced Lewis acid activity.

The positive activity of the catalyst is also maintained by protecting the catalyst from accelerated coke formation. A recycle stream of a hydrogen rich gas fraction previously described has been used to protect the catalyst from accelerated coke formation. The purity of the hydrogen recycle stream fraction has been controlled by purging the recycle gas and mixing the purged gas with a fuel gas for use in the system or purging to a system for hydrogen purification. The hydrogen system pressure is then maintained by supplying a makeup of relatively high purity hydrogen. The purge of hydrogen recycle gas and replenishment with high purity hydrogen gas makeup maintains the hydrogen partial pressure of the system which in turn maintains the catalyst activity to produce the desired approach to equilibrium of the $C_8$ alkyl isomers.

In accordance with the present invention, the system pressure is controlled by regulating the hydrogen makeup while eliminating a vapor purge of hydrogen recycle gas containing light hydrocarbon impurities. It will be appreciated that the increase in system pressure produced by not purging increases the hydrogen purity by increasing the solubility of the recycle gas light hydrocarbon impurities in the separator liquid. Since the vapor pressure of the hydrogen is higher than the hydrocarbons in the hydrogen recycle stream fraction, the hydrocarbons are selectively removed to increase recycle purity and hydrogen partial pressure without requiring purging. Accordingly, the chemical efficiency of the isomerization reaction is the same whether the hydrogen partial pressure is controlled by purging the hydrogen recycle gas to reduce light hydrocarbon impurities or if the system pressure is increased to purge the light hydrocarbons by increasing their solubility in the separator liquid. The light hydrocarbons removed from the recycle gas may then be subsequently recovered as a liquid and either used as a fuel in the process or sold as liquid petroleum gas and gasoline.

As a result, other than the hydrogen consumed by various chemical side reactions of the process, solution losses in the separator and a minor secondary venting in the hydrogen recycle compressor, only about 60% of the previously required hydrogen makeup gas is needed if no purging is performed thereby resulting in a substantial cost savings.

The activation and protection of a catalyst composite in accordance with the present invention provides approximately 50% reduction in the previously expected xylene ring loss of 6% of a conventional operation resulting in a substantial economic savings.

The method of recovering the $C_8$ isomer product from the reactor effluent is, in part, a function of the particular isomer desired. For example, if o-xylene is desired, it may be separated from the other isomers by fractional distillation, e.g., superfractionation, since its boiling point is sufficiently higher than the boiling point of the other $C_8$ alkyl aromatic hydrocarbons to permit effective separation by conventional distillation techniques. The remaining isomers can then be subjected to further isomerization by recycling them to the isomerization reactor. However, the m-xylene and p-xylene isomers are not readily separated from each other by distillation techniques because of these isomers' boiling points. They can be separated from each other by chemical separation techniques well known to the art such as sulfuric acid sulfonation, alkylation-dealkylation techniques, etc. In addition, p-xylene may be recovered by physical separation methods such as crystallization or adsorption-desorption.

The $C_8$ alkyl aromatic hydrocarbon-containing feedstock to the process of the present invention can be substantially pure $C_8$ alkyl benzene isomer, a mixture of $C_8$ alkyl benzene isomers, or hydrocarbon fractions rich in $C_8$ alkyl benzene isomers. For example, a source of $C_8$ alkyl benzene isomers is the $C_8$ aromatic fraction recovered from catalytic reformates, pyrolysis naphthas, or coal tars. The $C_8$ alkyl benzene fraction remaining after separating and recovering all or a part of a given isomer from such a source is a suitable $C_8$ alkyl aromatic-containing feedstock for the process of the invention. Thus, p-xylene, which is of growing importance, can be recovered from a $C_8$ catalytic reformate fraction by low temperature crystallization. The mother liquor produced from such low temperature crystallization is deficient in p-xylene with respect to the thermodynamic equilibrium concentration of $C_8$ alkyl benzene isomers and is an excellent $C_8$ alkyl aromatic-containing feedstock to the present process.

As will be recognized by one skilled in the art, the process of this invention utilizing the catalyst hereinbefore set forth, may be effected in any suitable manner and may comprise either a batch or continuous operation. The preferred method by which the process of this invention may be effected is the continuous type operation. Thus, a particularly preferred method of the fixed bed operation is one in which a non-equilibrium $C_8$ alkyl aromatic hydrocarbon fraction is continuously charged to the reaction zone containing the fixed bed of the desired catalyst, the zone being maintained at the proper operating conditions of temperature and pressure as described above. The reaction zone may comprise an unpacked vessel or coil or may be lined with an adsorbent packing material.

The documents, patents and patent applications referred to herein are hereby incorporated by reference.

Having described presently preferred embodiments of the invention, it is to be understood that it may be otherwise embodied within the scope of the appended claims.

What is claimed is:

1. A process for isomerizing a $C_8$ alkyl aromatic hydrocarbon-containing feedstock comprising the steps of:
   (a) providing a catalyst including platinum;
   (b) activating the catalyst by:
      (1) oxidizing the platinum of said catalyst in a reactor by circulating a stream of nitrogen containing about 1 percent by volume of oxygen across said catalyst while increasing the temperatures from ambient up to about 480° C.;
      (2) maintaining the circulating stream of nitrogen containing about 1 weight percent oxygen at a temperture of about 480° C. until the platinum of said catalyst is completely oxidized;
      (3) stopping the circulating stream and depressurizing the reactor;
      (4) purging the reactor with pure hydrogen at atmospheric pressure;
      (5) circulating pure hydrogen through the reactor over a range of conditions, slowly increasing temperature and pressure to a limit of less than about 340° C. at ambient pressure; and (6) stabilizing the catalyst by injecting ammonia into the reactor;

(c) contacting the feedstock in at least one isomerization zone with the catalyst and being effective to promote $C_8$ alkyl benzene isomerization at isomerization conditions in the presence of hydrogen at isomerization conditions to isomerize at least a portion of the $C_8$ alkyl aromatic hydrocarbons and to produce an effluent;

(d) separating the effluent to form a hydrogen-rich fraction, a first hydrocarbon-rich fraction containing benzene and toluene and having a lower average molecular weight relative to $C_8$ alkyl aromatic, and a second fraction enriched in $C_8$ alkyl aromatic content relative to the effluent;

(e) subjecting at least a portion of the first hydrocarbon-rich fraction to the contacting of step (c);

(f) increasing system pressure of the hydrogen rich fraction, said hydrogen rich fraction having vaporous light hydrocarbon impurities, said increase in system pressure being high enough to cause a phase change in the vaporous light hydrocarbon impurities from a vapor to a liquid phase, whereby said phase change causes an increase in hydrogen purity in the hydrogen rich fraction; and (g) recovering at least one $C_8$ alkyl aromatic product from the second fraction.

2. The process of claim 1 wherein said platinum is present in an amount of about 0.02% to about 3.0% by weight of said catalyst, calculated as elemental metal.

3. The process of claim 1 wherein said catalyst contains at least one aluminosilicate capable of promoting $C_8$ alkyl aromatic isomerization at the conditions of step (c), said aluminosilicate being present in an amount of about 1% to about 75% by weight of the total catalyst.

4. The process of claim 1 wherein the oxidized platinum component of said catalyst is reduced with pure hydrogen to platinum crystallites.

5. The process for isomerizing a $C_8$ alkyl aromatic hydrocarbon containing feedstock as recited in claim 4, wherein said system pressure is increased by regulating a hydrogen makeup of said hydrogen rich fraction and by eliminating a vapor purge on said hydrogen rich fraction.

6. A process for isomerizing ethylbenzene to xylene, comprising the steps of:

(a) providing a catalyst including at least one metal component;

(b) activating the catalyst by:
(1) oxidizing the metal component of said catalyst in a reactor by circulating a stream of nitrogen containing about 1 percent by volume of oxygen across said catalyst while increasing the temperatures from ambient up to about 480° C.;
(2) maintaining the circulating stream of nitrogen containing about 1 weight percent oxygen at a temperature of about 480° C. until the metal component of said catalyst is completely oxidized;
(3) stopping the circulating stream and depressurizing the reactor;
(4) purging the reactor with pure hydrogen at atmospheric pressure;
(5) circulating pure hydrogen through the reactor over a range of conditions to a maximum of about 340° C. at ambient pressure; and
(6) stabilizing the catalyst by injecting ammonia into the reactor;

(c) contacting the feedstock in at least one isomerization zone with the catalyst and being effective to promote $C_8$ alkyl benzene isomerization at isornerization conditions in the presence of hydrogen at isomerization conditions to isomerize at least a portion of the $C_8$ alkyl aromatic hydrocarbons and to produce an effluent;

(d) separating the effluent to form a hydrogen-rich fraction, a first hydrocarbon-rich fraction containing benzene and toluene and having a lower average molecular weight relative to $C_8$ alkyl aromatic, and a second fraction enriched in $C_8$ alkyl aromatic content relative to the effluent;

(e) subjecting at least a portion of the first hydrocarbon-rich fraction to the contacting of step (c);

(f) increasing system pressure of the hydrogen rich fraction, said hydrogen rich fraction having vaporous light hydrocarbon impurities, said increase in system pressure being high enough to cause a phase change in the vaporous light hydrocarbon impurities from a vapor to a liquid phase, whereby said phase change causes an increase in hydrogen purity in the hydrogen rich fraction; and (g) recovering at least one $C_8$ alkyl aromatic product from the second fraction.

7. A process for isomerizing a $C_8$ alkyl aromatic hydrocarbon-containing feedstock, comprising the steps of:

(a) providing a catalyst including at least one metal component;

(b) activating the catalyst by:
(1) oxidizing the metal component of said catalyst in a reactor by circulating a stream of nitrogen containing about 1 percent by volume of oxygen across said catalyst while increasing the temperatures from ambient up to about 480° C.;
(2) maintaining the circulating steam of nitrogen containing about 1 weight percent oxygen at a temperature of about 480° C. until the metal component of said catalyst is completely oxidized;
(3) stopping the circulating stream and depressurizing the reactor;
(4) purging the reactor with pure hydrogen at atmospheric pressure;
(5) circulating pure hydrogen through the reactor over a range of conditions to a maximum of about 340° C. at ambient pressure;
(6) analyzing the reactor contents for the occurrence of water in the reactor;
(7) stabilizing the catalyst by injecting ammonia into the reactor upon the detection of water in the reactor;

(c) contacting the feedstock in at least one isomerization zone with the catalyst and being effective to promote $C_8$ alkyl benzene isomerization at isomerization conditions in the presence of hydrogen at isomerization conditions to isomerize at least a portion of the $C_8$ alkyl aromatic hydrocarbons and to produce an effluent;

(d) separating the effluent to form a hydrogen-rich fraction, a first hydrocarbon-rich fraction containing benzene and toluene and having a lower average molecular weight relative to $C_8$ alkyl aromatic, and a second fraction enriched in $C_8$ alkyl aromatic content relative to the effluent;

(e) subjecting at least a portion of the first hydrocarbon-rich fraction to the contacting of step (c);

(f) increasing system pressure of the hydrogen rich fraction, said hydrogen rich fraction having vaporous light hydrocarbon impurities, said increase in system pressure being high enough to cause a phase change in the vaporous light hydrocarbon impurities from a vapor to a liquid phases whereby said phase change causes an increase in hydrogen purity in the hydrogen rich fraction; and (g) recovering at least one $C_8$ alkyl aromatic product from the second fraction.

8. The process of claim 7 wherein said metal component is selected from the group consisting of platinum group metal component and mixtures thereof and said platinum group metal component is present in an amount of about 0.02% to about 3.0% by weight of said catalyst, calculated as elemental metal.

9. A process for isomerizing a $C_8$ alkyl aromatic hydrocarbon-containing feedstock, including the isomerization of ethylbenzene to xylene, comprising the steps of:

(a) providing a catalyst including at least one metal component;

(b) activating the catalyst by:

(1) oxidizing the metal component of said catalyst in a reactor by circulating a stream of nitrogen containing about 1 percent by volume of oxygen across said catalyst while increasing the temperatures from ambient up to about 480° C.;

(2) maintaining the circulating stream of nitrogen containing about 1 weight percent oxygen at a temperature of about 480° C. until the metal component of said catalyst is completely oxidized;

(3) stopping the circulating stream and depressurizing the reactor;

(4) purging the reactor with pure hydrogen at atmospheric pressure;

(5) circulating pure hydrogen through the reactor over a range of conditions to a maximum of about 340° C. at ambient pressure; and (6) stabilizing the catalyst by injecting ammonia into the reactor to minimize the conversion of Brônstead acid sites to Lewis acid cites to maximize the efficiency of the isomerization of ethylbenzene to xylene;

(c) contacting the feedstock in at least one isomerization zone with the catalyst and being effective to promote $C_8$ alkyl benzene isomerization at isomerization conditions in the presence of hydrogen at isomerization conditions to isomerize at least a portion of the $C_8$ alkyl aromatic hydrocarbons and to produce an effluent;

(d) separating the effluent to form a hydrogen-rich fraction, a first hydrocarbon-rich fraction containing benzene and toluene and having a lower average molecular weight relative to $C_8$ alkyl aromatic, and a second fraction enriched in $C_8$ alkyl aromatic content relative to the effluent;

(e) subjecting at least a portion of the first hydrocarbon-rich fraction to the contacting of step (c);

(f) increasing system pressure of the hydrogen rich fraction, said hydrogen rich fraction having vaporous light hydrocarbon impurities, said increase in system pressure being high enough to cause a phase change in the vaporous light hydrocarbon impurities from a vapor to a liquid phase, whereby said phase change causes an increase in hydrogen purity in the hydrogen rich fraction; and (g) recovering at least one $C_8$ alkyl aromatic product from the second fraction.

10. The process of claim 9 wherein said metal component is selected from the group consisting of platinum group metal component and mixtures thereof and said platinum group metal component is present in an amount of about 0.02% to about 3.0% by weight of said catalyst, calculated as elemental metal.

11. A process for isomerizing a $C_8$ alkyl aromatic hydrocarbon-containing feedstock, including the isomerization of ethylbenzene to xylene, comprising the steps of:

(a) providing a catalyst including platinum;

(b) activating the catalyst;

(c) contacting the feedstock in at least one isomerization zone with the catalyst and being effective to promote $C_8$ alkyl benzene isomerization at isomerization conditions in the presence of hydrogen at isomerization conditions to isomerize at least a portion of the $C_8$ alkyl aromatic hydrocarbons and to produce an effluent;

(d) separating the effluent to form a hydrogen-rich fraction, a first hydrocarbon-rich fraction containing benzene and toluene and having a lower average molecular weight relative to $C_8$ alkyl aromatic, and a second fraction enriched in $C_8$ alkyl aromatic content relative to the effluent;

(e) subjecting at least a portion of the first hydrocarbon-rich fraction to the contacting of step (c);

(f) increasing system pressure of the hydrogen rich fraction, said hydrogen rich fraction having vaporous light hydrocarbon impurities, said increase in system pressure being high enough to cause a phase change in the vaporous light hydrocarbon impurities from a vapor to a liquid phase, whereby said phase change causes an increase in hydrogen purity in the recycle stream; and (g) recovering at least one $C_8$ alkyl aromatic product from the second fraction.

12. The process for isomerizing a $C_8$ alkyl aromatic hydrocarbon containing feedstock as recited in claim 11, wherein said system pressure is increased by regulating a hydrogen makeup of said hydrogen rich fraction and by eliminating a vapor purge on said hydrogen rich fraction.

13. The process for isomerizing a $C_8$ alkyl aromatic hydrocarbon containing feedstock as recited in claim 11, further comprising the step of recovering light hydrocarbon impurities in the liquid phase.

* * * * *